United States Patent [19]

Senda et al.

[11] Patent Number: 4,820,399
[45] Date of Patent: Apr. 11, 1989

[54] ENZYME ELECTRODES

[75] Inventors: Mitsugi Senda; Tokuji Ikeda; Isao Katasho, all of Kyoto, Japan

[73] Assignee: Shimadzu Corporation, Kyoto, Japan

[21] Appl. No.: 770,202

[22] Filed: Aug. 28, 1985

[30] Foreign Application Priority Data

| Aug. 31, 1984 [JP] | Japan | 59-183124 |
| Aug. 31, 1984 [JP] | Japan | 59-183125 |
| Dec. 17, 1984 [JP] | Japan | 59-266941 |
| Dec. 17, 1984 [JP] | Japan | 59-266942 |

[51] Int. Cl.$^4$ .......................................... G01N 27/54
[52] U.S. Cl. .................................. 204/403; 204/415; 435/9; 435/817
[58] Field of Search ....................... 204/1 E, 403, 415; 435/9, 817

[56] References Cited

U.S. PATENT DOCUMENTS

| 3,838,033 | 9/1974 | Mindt et al. | 204/403 |
| 4,073,713 | 2/1978 | Newman | 204/403 |
| 4,224,125 | 9/1980 | Nakamura et al. | 204/403 |
| 4,321,123 | 3/1982 | Nakamura et al. | 204/403 |
| 4,356,074 | 10/1982 | Johnson | 435/817 |
| 4,406,066 | 9/1983 | Johnson | 435/190 |
| 4,490,464 | 12/1984 | Gorton et al. | 204/403 |
| 4,545,382 | 10/1985 | Higgins et al. | 204/403 |
| 4,556,635 | 12/1985 | Hitzman et al. | 204/403 |

FOREIGN PATENT DOCUMENTS 0051595 4/1979 Japan ................................ 204/403

OTHER PUBLICATIONS

Toluji Ikeda, Isao Katasho, Masugu Kamei and Mitsugi Senda, "Electrocatalysis with a Glucose-Oxidase-Iommobilized Graphite Electrode," Agric. Biol. Chem 48(8).

Tokuji Ikeda, Shinji Ando, and Mitsugi Senda, "Electrochemical Oxidation-Reduction Properties of Covalently Bound FAD of Cholesterol Oxidase Adsorbed on Mercury Electrode Surface," Bull, Chem. Soc. Jpn, 54, 1981, pp. 2189-2193.

Shinji Ando, Tokuji Ikeda, Tadaaki Kakutani and Mitsugi Senda, "Theory of Stationary Current-Potential Curves at Redox Catalyst Electrode," Rev. Polarog. (Kyoto), 26:19 (1980).

Primary Examiner—John F. Niebling
Assistant Examiner—Ben C. Hsing
Attorney, Agent, or Firm—Sandler & Greenblum

[57] ABSTRACT

An enzyme electrode composed of a carrier, an enzyme immobilized on a parr of the surface of the carrier, a coating film consisting of a thin film coating the portion where the enzyme is immobilized and being permeable for the substrate for the enzyme and an internal electrode capable of applying voltage to the surface where the enzyme is immobilized, said carrier being impregnated with a substance which acts as an electron transfer mediator, which is useful for measurement of concentration of the substrate in vital samples such as blood serum, blood plasma, urine etc.

13 Claims, 13 Drawing Sheets

E/volt vs. SCE

E/volt vs. SCE

ENZYME ELECTRODES

BACKGROUND OF THE INVENTION

1. Field of the Invention

The present invention relates to enzyme electrodes. More particularly, it relates to electrodes for amperometrically measuring concentrations in an electrolyte of those substances which can be the substrate for oxidases, such as glucose, galactose and the like, or of those substances which can be the substrate for dehydrogenases, such as lactic acid, alcohol, glycerol and the like.

2. Description of the Prior Art

In recent years, increasing attention has been paid to oxidoreductase immobilized electrodes (hereinafter, referred to as enzyme electrodes) (reference is made to T. Ikeda, S. Ando, and M. Senda, Bull. Chem. Soc. Jpn., 54, 2189 (1981)). These electrodes behave as a substitute for a chemical electron transporter in enzyme reaction, and it has been suggested that they could be utilized in such novel applications as enzyme electrodes, detectors in flowing systems biochemical fuel cells and enzyme reactors (reference is made to S. Ando, T. Ikeda, T. Kakutani, and M. Senda, Rev. Polarogr. (Kyoto), 26, 19(1980): abstracts of papers presented at the Annual Meeting on Polarography, October 1980, Fukuoka).

Such enzyme electrodes are of the form directly utilizing current (electric current and voltage related to enzyme reaction, being different from those electrodes of the form indirectly estimating the amount of substrate contributing to enzyme reaction by measuring the amount of a product produced by the enzyme reaction, for example, the amount of hydrogen peroxide generated, with the so-called oxygen electrode or platinum electrode whose sensitive surface is coated with an enzyme-immobilized film.

In this regard, the inventors of the present invention have previously found that glucose oxidase-immobilized electrodes using graphite as a carrier can function as a bioelectrocatalysis electrode for electro-oxidation of glucose in the presence of an electron transfer mediator such as p-benzoquinone in solution (reference is made to T. Ikeda, I. Katasho, M. Kamei, and M. Senda, Agric. Biol. Chem., 48, (8) (1984)).

In such oxidase electrodes, however, there were problems on practical use. For example, (a) it was required to add to the solution to be measured a substance working as the electron transfer mediator participating in the enzyme reaction, at every time of measurement, (b) since the amount of such substance capable of contributing to the reaction was regulated by its concentration in the solution and this varied by concentration polarization during electrolysis, the substance could not be supplied to the reaction system in a high and constant concentration and accordingly the response speed and the sensitivity were insufficient, and (c) the influence on the substance of these substances coexisting in the solution to be measured, pH of the solution, oxygen contained in the solution, etc., as well as that of light, could not be disregarded.

On the other hand, it has been also suggested to form an oxidation-reduction system by utilizing immobilized dehydrogenase in combination with nicotinamide adenine dinucleotide (NAD) as an electron transfer mediator and use the system for an electrode reaction. Moreover, in order to carry out the measurement without adding the NAD to the solution to be measured at every time of measurement as described above, it has been tried to immobilize NAD together with enzyme. As representatives of such trials ① electrodes prepared by trapping a NAD-high molecular weight compound obtained by chemically binding NAD with a high molecular weight compound, such as agarose or dextran, on the inside surface of a suitable substrate-permeable film together with enzyme and fixing the film to a platinum or graphite electrode, ② electrodes prepared by chemically binding NAD directly with a substrate-permeable film, trapping enzyme on the inside surface of the film and simultaneously fixing the film to a platinum or graphite electrode, ③ electrodes prepared by applying chemical treatment to a substratepermeable film to make it hardly permeable for NAD, trapping enzyme on the inside surface of the film and fixing the film to a platinum or graphite electrode, and the like have been suggested.

However, the above-described enzyme electrodes ① and ② involved the problem that the enzyme reactivity of NAD itself was largely decreased by incorporation of NAD into a high molecular weight compound, and the electrodes ③ involved the problem that leakage of NAD could not be prevented perfectly and the enzyme reactivity lowered as time passed.

The present invention is one which is made in view of various problems as mentioned above, and one of its purposes is to provide enzyme electrodes capable of maintaining a high reactivity of immobilized enzyme for a long period of time without adding any electron transfer mediator to the solution to be measured.

SUMMARY OF THE INVENTION

Thus, the present invention provides an enzyme electrode composed of a carrier, an enzyme immobilized on a part of the surface of the carrier, a coating film consisting of a thin film coating the portion where the enzyme is immobilized and being permeable for the substrate for the enzyme, and an internal electrode capable of applying voltage to the surface where the enzyme is immobilized, said carrier being impregnated with a substance which acts as an electron transfer mediator.

Such enzyme electrodes of the present invention are useful for measurement of concentrations of the substrate in vital samples such as blood serum, blood plasma, urine, etc. or in enzyme reactors, and also valuable as electrodes for enzyme reactors or fuel cells.

DESCRIPTION OF THE PREFERRED EMBODIMENT

Figure 1:
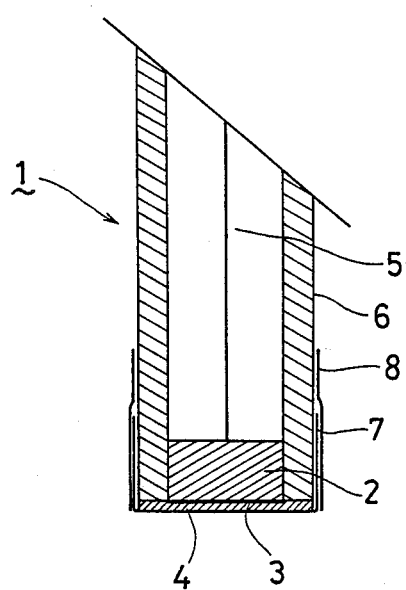
FIG. 1, FIG. 6, FIG. 13 and FIG. 16 are each a diagram showing the construction of an embodiment of enzyme electrodes of the present invention.

The enzyme electrodes of the present invention are usually used by setting an electrolysis system wherein the enzyme electrodes are used as the anode with an enzyme-immobilized surface (a substrate-sensitive surface) kept in contact with, or dipped in, the solution to be measured. That is, the enzyme electrodes of the present invention can be used as an amperometric electrode, especially as a sensor. In these cases, there is no special limitation on the cathode (the counter-electrode), and various electrodes such as platinum electrode, silver/silver chloride electrode, mercury/mercurous chloride electrode, etc. can be used as the cathode. The measurement as sensor is usually effected according to the controlled-voltage electrolysis.

The electrodes of the present invention are usually in the form that a carrier is buried at a terminal portion of a cylindrical insulator as the supporting material for the sensor, the substrate-sensitive portion is formed on the exposed surface of the carrier, and an internal electrode and lead wires are suitably provided. However, they may be in any other form (for example, the form that they are incorporated directly in a flowing passage) in accordance with their use, as far as the substrate-sensitive portion constitutes the electrode. If desired, the counter-electrode can be incorporated in the same supporting material for sensor.

The most characteristic feature of the present invention resides in the point that the carrier for immobilizing enzyme is impregnated with a substance which can be the electron transfer mediator for enzyme reaction. As a result of such impregnation, the electron transfer mediator is well supplied in a high concentration to the enzyme-immobilized surface. Since the electron transfer mediator consumed by the enzyme reaction regenerated by the electrode reaction, any net consumption does not occur by reaction. Further, even if the electron transfer mediator leaked out through the coating film of the enzyme surface, it is supplied from the carrier as a storage layer for the transfer mediator in high concentration. Therefore, the concentration of the electron transfer mediator at the enzyme-immobilized surface is kept substantially constant. Thus, the intended enzyme reaction can be performed along with the electrode reaction without adding the electron transfer mediator to the solution to be measured, and without any lowering in the enzyme reaction activity.

As the carrier of the enzyme electrodes of the present invention, one having at least a surface capable of fixing the enzyme physically or chemically and being in a form capable of being impregnated with an electron transfer mediator as described hereinafter is selected. To be concrete, one in the form of porous material, paste or gel is used. As the porous material, it is preferable to use a porous molding of a conductive or semi-conductive substance, such as sintered material or sponge, which is processed into the desired form. As the paste or the gel, it is preferred because of the ease of forming the internal electrode to use a paste or gel containing a conductive or semi-conductive powder. As examples of the conductive substance, graphite and nobel metals such as gold, platinum, etc. are mentioned. As the semi-conductive substance, inorganic compounds such as titanium oxide, tin oxide, etc. are mentioned. Further, the so-called conductive high molecular weight compounds (high molecular electroconductive materials) can be used as the conductive or semi-conductive substance, and as examples of them there can be mentioned polyacetylenes, polypyrrole, polythiophene, polyselenophene, poly-p-phenylene sulfide poly-p-phenylene selenide, poly-p-phenylene oxide, polyaniline, etc. which are provided with a suitable conductivity by doping.

As preferred examples of the above porous molding, there can be mentioned porous graphite.

As preferred examples of the above paste or gel, there can be mentioned a paste or gel obtained by mixing graphite powder or a noble metal powder with a nonpolar binder such as liquid paraffin, undecane, Teflon paste, silicon grease, white vaseline, etc. and, if necessary, a viscosity-increasing agent such as cellulose powder and/or a high molecular weight gelling agent. The amount of the above conductive or semi-conductive substance powder is suitably 60–70% by weight of the whole, in view of form or shape maintenance. The particle diameter of the powder is suitably about 1 $\mu$m–50 $\mu$m.

However, even a paste or gel not containing any conductive or semi-conductive substance powder may be used as the carrier of the electrodes of the present invention, as is illustrated by Example 10. Likewise, the porous material may also be constituted with an insulating substance (such as resins or ceramics). It is also possible to use an aggregate of fibers such as carbon fibers as the carrier.

Such carrier acts as a sort of storage layer for the electron transfer mediator, and its capacity is properly decided according to the term of use and the ease of treatment of the enzyme electrode.

Impregnation of the carrier as described above with a substance which acts as the electron transfer mediator can be performed easily when the carrier is a paste or gel by directly admixing the substance to the paste or gel as it is prepared. On the other hand, when the carrier is a porous material, the impregnation can be performed easily by dipping the porous material in a liquid dispersion of the substance or preferably in a sol for the above-mentioned paste or gel, or by applying the liquid dispersion or the sol to the porous material. That is, the porous material is impregnated with the substance which acts as the electron transfer mediator, in the form of the above mentioned paste or gel. When an aggregate of fibers is used as the carrier, the impregnation in the form of paste or gel may be performed according to the same manner as that employed for the porous material.

As the electron transfer mediator with which the carrier as described above is impregnated, various compounds which participate in the reaction as an electron acceptor in the presence of an immobilized enzyme and a substrate for it and are capable of being kept stable in the carrier, particularly in a binder for a paste or gel, can be used. As preferable electron transfer mediators for oxidases, there can be mentioned p-benzoquinones, ubiquinones, potassium ferricyanide, dichlorophenolindophenol (DCIP), phenazine methosulfates (PMS) and the like. The amount of impregnation is suitably 0.2-30% by weight when p-benzoquinone is used to a graphite paste. A content in a graphite paste of less then 0.2% by weight is not preferable in respect of current sensitivity, and a content more than 30% by weight is not preferable in respect of shape maintenance of electrodes and of economical reason. The most preferable content is 15-25% by weight.

As preferable electron transfer mediators for dehydrogenases, there can be mentioned NAD and dichlorophenolindophenol (DCIP). Besides these compounds, however, any compounds which participate in the reaction as an electron acceptor in the presence of a dehydrogenase and a substrate for it and are stable in the carrier, especially in the paste or gel are suitable. The amount of impregnation with such electron transfer mediator is suitable 1-10% by weight when NAD is used in a graphite paste. A content in a graphite paste of less than 1% by weight is not preferable with respect to current sensitivity, and a content more than 10% by weight is not preferable with respect to shape maintenance of electrodes and for economical reasons. The most preferable content is 3-5% by weight.

The enzyme immobilized on the carrier as described above can be selected properly in accordance with the substrate whose detection or conversion is intended. When an oxidase is used, glucose oxidase/glucose, galactose oxidase/galactose, alcohol oxidase/alcohol cholesterol oxidase/cholesterol, amino acid oxidase/amino acid, uric acid oxidase/uric acid, etc. are representative of the enzyme/substrate combinations.

As other enzyme/substrate combinations, there can be mentioned alcohol dehydrogenase/alcohol, glucose dehydrogenase/glucose, glutamate dehydrogenase/glutamic acid, lactic acid dehydrogenase/lactic acid, glycerol dehydrogenase/glycerol and the like.

The immobilization of such enzymes on the carrier is performed usually by a solution method, that is, by simply applying or dropping an enzyme solution to or onto a surface of carrier and evaporating the solvent from the solution held on the surface. In this case, it is preferred to make the surface as smooth as possible beforehand. The amount of immobilized enzyme is preferably about 10-200 $\mu g/cm^2$ in the case of alcohol dehydrogenase or glucose oxidase. Of course, the immobilization may be effected in any other method (such as chemical binding), as the case may be.

The substrate-permeable thin film of the present invention serves for holding and fixing the enzyme adhered or fixed onto the surface of carrier and for protecting the enzyme from the external environment. As such permeable film to coat at least the portion where the enzymes are immobilized, there may be used cellulose acetate film, nitrocellulose film, K-carrageenan gel film, polyacrylamide gel film, dialysis film and the like. A nitrocellulose film formed by spreading and drying a solution containing collodion is preferably employed. Although there is no limitation on the thickness of film, it can be generally said that a thinner film is suitable for shortening the response time and a thicker one is favorable for broadening the range of response concentration. Usually, a thickness of about 20-500 $\mu m$ is suitable, although it depends on the type of film.

The internal electrode capable of applying voltage to the enzyme immobilized surface can be a filamentary one which is generally used, or a plane one. For instance, when a porous material, or a paste or gel, of a conductive or semiconductive substance, is used as the carrier, it is possible to supply voltage to the enzyme immobilized surface by connecting a filamentary electrode at least to said carrier. When a porous material, or a paste or gel, not using a conductive or semi-conductive substance is employed as the carrier, it is preferred to use a plane electrode, especially a grid electrode having many spaces or of reticular form, and to laminate it on the portion of the carrier where enzyme is immobilized, to form an internal electrode. The grid electrode having many spaces is a preferable embodiment, because it is possible by employing it to prevent superfluous permeation or elution onto the carrier surface of the electron transfer mediator in the carrier.

Hereinafter, the present invention is further explained in detail by giving Examples which however shall never constitute any restriction on the invention:

EXAMPLE 1

A glucose oxidase electrode using glucose oxidase as enzyme and p-benzoquinone as electron transfer mediator (A) Preparation of Electrode Reagents Glucose oxidase (GOD)

Type II, a product of Sigma Co. (EC 1,1,3,4 derived from Aspergillus Niger).

p-Benzoquinone (BQ)

A product of Wako Pure Chemical Co. (purified by sublimation before use).

Collodion solution (5%)

A product of Wako Pure Chemical Co..

Liquid Paraffin

A product of E. Merck Co..

Graphite powder

No. ACP, a product of Nippon Kokuen Co..

A prescribed amount of p-benzoquinone was mixed with 3 ml of liquid paraffin, and then 5 g of graphite powder was further added to the mixture. The p-benzoquinone/graphite paste thus obtained was packed into one end of a glass tube of 3.4 mm inner diameter. The surface of exposed paste was smoothed by means of a piece of wax-paper to form a paste electrode (the carrier) having a surface area of $9.0 \times 10^{-2}$ cm$^2$.

Next, an aqueous GOD solution of a prescribed concentration was dropped by a syringe on the surface of said paste electrode, and then the solvent was evaporated from the solution hold on the surface. Thereafter, 20 μl of a collodion/ethanol (1:4 volume/volume) mixture was spread on the surface and dried to form a thin film of nitrocellulose on the surface of the electrode.

To the electrode (the carrier) thus obtained, an outgoing electrode (the internal electrode) consisting of platinum wire was provided. By further setting a nylon net and a teflon tube for supporting the nitrocellulose film, a glucose oxidase electrode (a GOD-immobilized/benzoquinone-graphite paste electrode) (1) of the present invention as shown in FIG. 1 was prepared. In FIG. 1, (2) denotes the p-benzoquinone/-graphite paste electrode (the carrier), (3) denotes the immobilized GOD, (4) denotes the thin nitrocellulose film, (5) denotes the platinum wire, (6) denotes the glass tube, (7) denotes the nylon net and (8) denotes the heat shrinkable teflon tube.

The electrode was washed several times with distilled water and stored overnight in an acetate buffer solution having a pH 5.0 before it was used.

(B) Cyclic Voltammetry

Voltammetry by the three-electrode method was effected using the above-described glucose oxidase electrode. Condition of the measurement were as follows:

Instruments

Potentiostat (made by Fuso Co.)
Signal generator (HB-104, made by Hokuto Electric Co.)
Counter-electrode (platinum plate)
Referential electrode (saturated calomel electrode)
Recorder (X-Y recorder, made by Yokogawa Electric Co.)

Electrolyte

Deoxygenated 0.1 M acetate buffer solution having a pH 5.0
Temperature: $23 \pm 1°$ C.
Stirring rate: 500 r.p.m.

Results

Figure 2A:
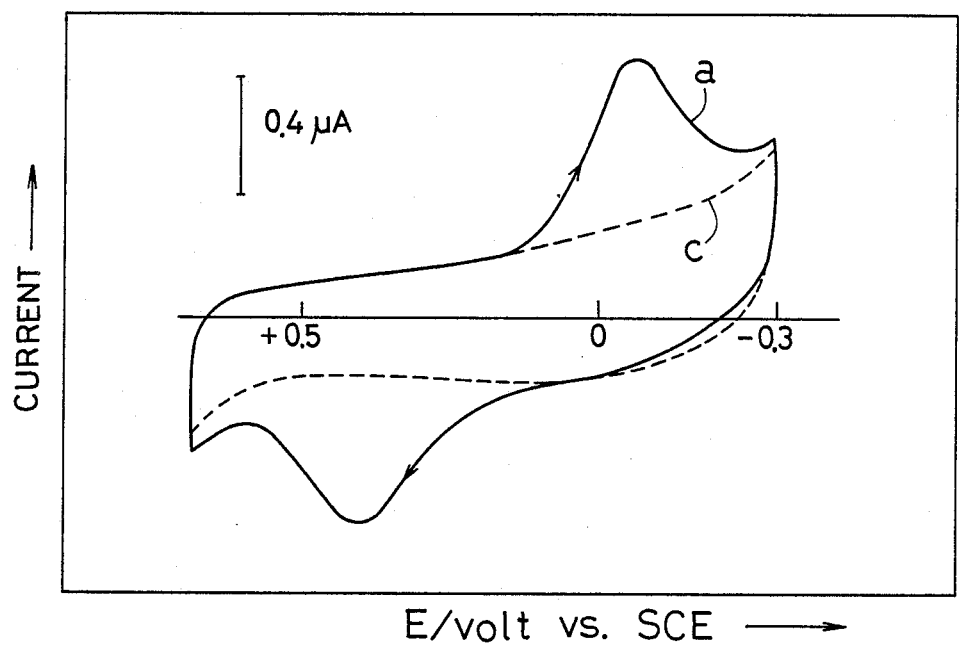
FIG. 2A and FIG. 2B are each a graph showing the cyclic voltammogram pertaining to the enzyme electrode of Example 1, A being for the case wherein glucose is not added and B being for the case wherein 41 mM glucose is added. In these Figures, the broken lines c and d are for electrodes not containing p-benzoquionone in paste (electrodes of the Referential Examples) and the full line a and b are for electrodes of the present invention.

An electrode of the present invention prepared by immobilizing 18 μg of GOD on a graphite paste electrode containing 0.25% by weight of p-benzoquinone was immersed in the above-described acetate buffer solution and the cyclic voltammogram was recorded at a potential scan rate of 50 mV/s. As shown by the full line in FIG. 2A, the peak potentials were noted at $-0.07$ V and $+0.40$ V (vs SCE) in cathodic and anodic waves, respectively. Although the cyclic potential scan was continued further for several hours, any decrease in the current was not observed. As an electrode similar to this, but not containing p-benzoquinone, was estimated in the same manner as that mentioned above, any voltammetric peak was not observed as shown by the broken line in FIG. 2A.

Thus, it became apparent that the voltammetric peak are ascribed to the electrochemical redox reaction of p-benzoquinone which has moved from the paste to the interfacial space between the graphite paste electrode (the carrier) and the thin nitrocellulose film, and the p-benzoquinone molecules contribute to the electrochemical reduction reaction.

Although p-benzoquinone might slowly leak out through the thin nitrocellulose film into the electrolyte, p-benzoquinone is supplied from the graphite paste medium so that the concentration of p-benzoquinone at the interface between the graphite paste and the thin nitrocellulose film is kept substantially constant.

(C) Electrocatalytic Oxidation of Glucose

Figure 2B:
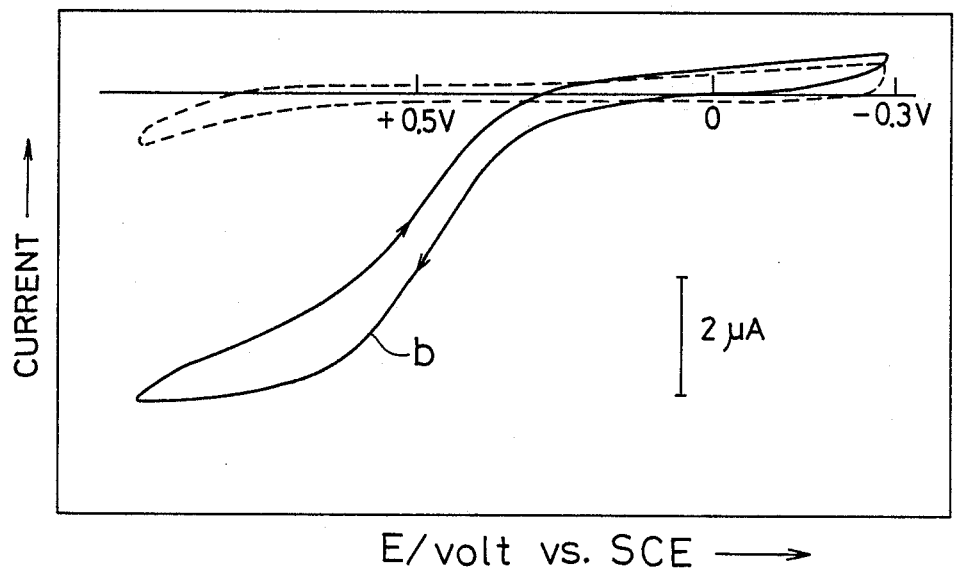
Figure 3A:
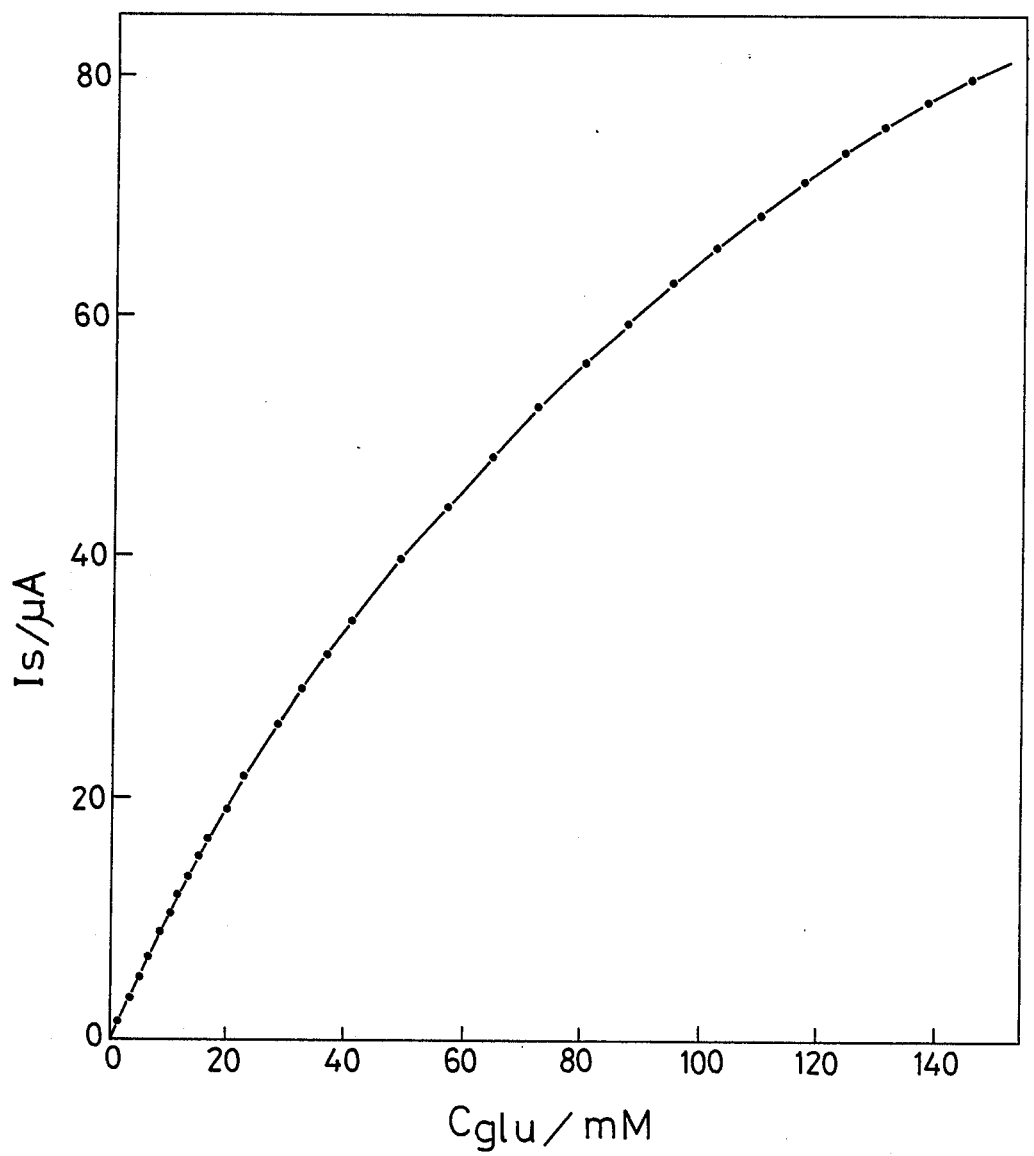
FIG. 3A and FIG. 3B are each a graph showing the relation between glucose concentration and anode current Is at an applied voltage of 0.5 V, with regard to the electrode of Example 1.
Figure 3B:
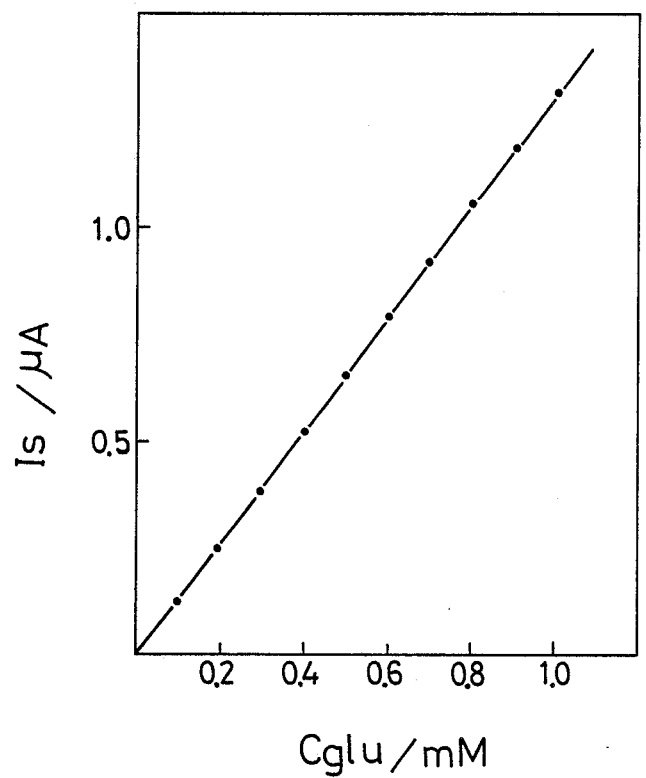

When glucose was added to the above-described buffer solution, it was observed that the anodic current of the electrode of the present invention was significantly increased as shown by the full line in FIG. 2B, and that the steady-state current Is at a given potential increased as the concentration of glucose in solution measured was increased, as shown in the FIGS. 3A and 3B. It was found that the current Is increased with the increasing content of p-benzoquinone in the graphite paste within the range of 0.25–10% by weight and it approached almost a limiting value as the content exceeded 10% by weight. The current Is depended also on the amount of GOD applied on the surface of the carrier. For example, paste electrodes containing 20% by weight of p-benzoquinone on which 1.8 μg and 18 μg of GOD were immobilized produced currents Is of 2 μA and 32 μA, respectively.

These results indicate that GOD immobilized on the surface of electrodes maintains activity and that p-benzoquinone entrapped at the interface acts as an electron transfer mediator between the immobilized GOD and the paste electrode.

As to a p-benzoquinone (30% by weight)/graphite paste electrode on which 18 μg of GOD is immobilized, the dependency of Is at an impressed voltage of 0.5 V on the glucose concentration (Cglu) is shown in FIGS. 3A and 3B. The maximum current Is$^{max}$ and the apparent Michaelis constant were determined to be 124 μA and 104 mM, respectively, from the intercept and the slope of the double reciprocal plot of the data in FIGS. 3A and 3B. From this Is$^{max}$ value, it is estimated that the amount of electrocatalytically active GOD immobilized on the carrier is $3 \times 10^{-11}$ mol/cm$^2$ which corresponds to about 3% of the total amount of GOD used, when the catalytic activities were assumed to be the same for both immobilized GOD molecules and GOD molecules dissolved in the solution measured.

The above electrode showed a linear current response to the glucose concentration, up to the concentration of 15 mM, with a correlation coefficient of 0.9999. Since the background current was very small ($0.2 \pm 0.01$ μA), it was possible to determine glucose concentrations lower than 1 mM with a coefficient of variation of 5.3% (n=5) at Cglu=1 mM (reference is made to FIG. 3B). The response of current was fast and the steady-state current was reached within 20 seconds.

As the stability of the electrode was evaluated by periodically testing its response to 8.3 mM glucose, it was found that its original activity was retained for more than a week, the electrode being stored in the buffer solution at temperatures lower than 5° C. when not in use.

As the reproducibility of preparing the electrode was evaluated by the response to 8.3 mM glucose, with regard to four sensors prepared by immobilizing 18 μg of GOD on p-benzoquinone (30% by weight)/graphite paste electrodes, they gave an average Is value of 7.9 μA with a standard deviation of 0.7 μA.

Figure 4:
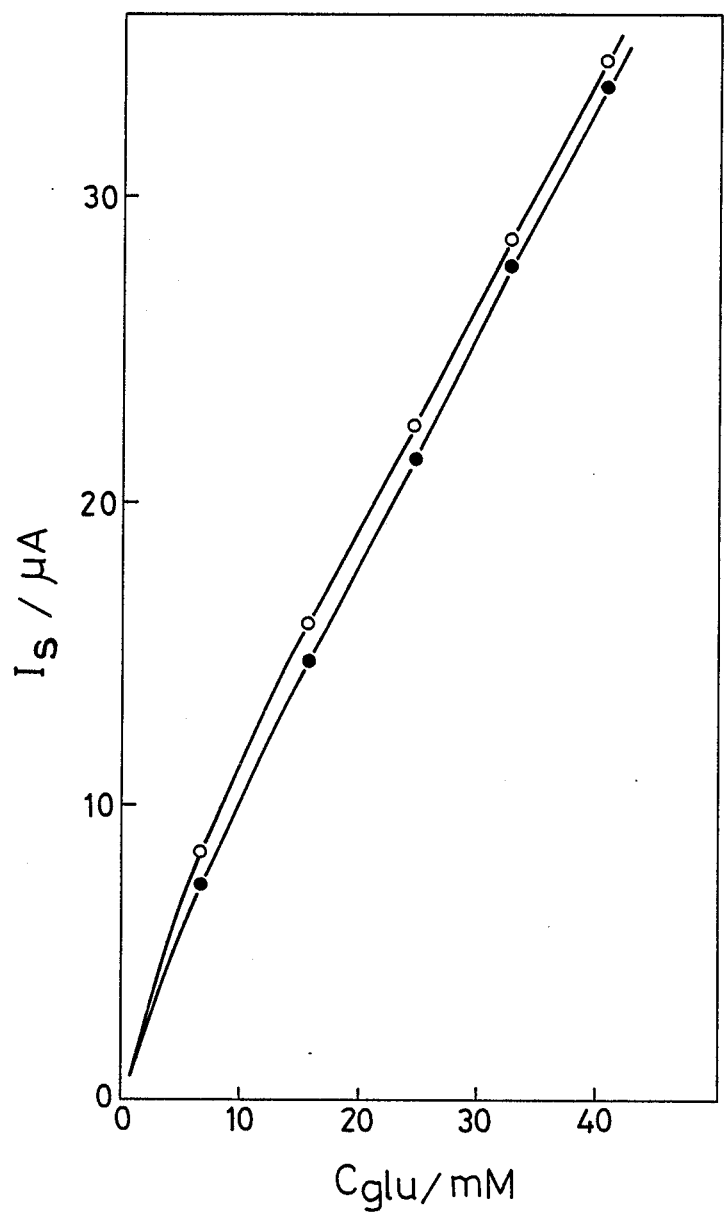
FIG. 4 is a graph showing the relation between glucose concentration and anode current Is at the same applied voltage of 0.5 V, the plot o being for a deaerated solution and the plot • being for an air-saturated solution.

In order to evaluate the influence of oxygen, Is of an air-saturated solution and Is of a deaerated solution were measured with respect to solutions containing 5–40 mM of glucose. The results are shown in FIG. 4. It was found that the influence was small over the studied range of glucose concentration, which covered the glucose concentrations usually detected in blood samples.

These electrodes of the present invention work suitably in solutions having a pH within the range 5 to 8.

EXAMPLE 2

A glucose oxidase electrode was prepared in the same manner as Example 1, except that potassium ferricyanide was used instead of p-benzoquinone as the electron acceptor.

Figure 5:
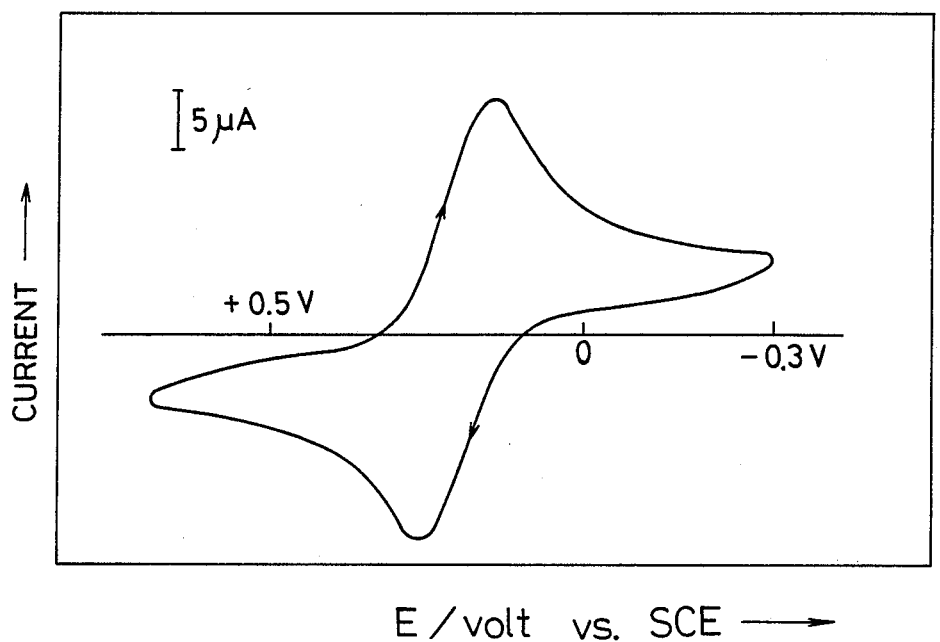
FIG. 5 is a graph showing the cyclic voltammogram of the glucose oxidase electrode of Example 2.

With this electrode, the same cyclic voltammetry was effected in the same manner as Example 1. As shown in FIG. 5, voltammetric peaks were observed. Thus, it was apparent that potassium ferricyanide contributed to the electrochemical reaction.

EXAMPLE 3

Figure 6:
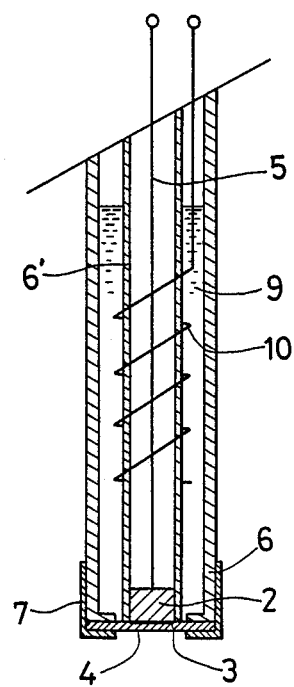

An electrode of such constitution as the counter-electrode was set inside the glass tube (1) which was prepared according to the manner as described in Example 1 (A). The constitution of the electrode is shown in FIG. 6, wherein (10) denotes a silver/silver chloride electrode constituting the counterelectrode (cathode), which winds around the inner supporting material (6′) and is fixed thereon, (9) denotes the solution inside the electrode, consisting of acetate buffer solution containing potassium chloride, and other numerical figures correspond to those described before.

EXAMPLE 4

Alcohol Dehydrogenase Electrode

An alcohol dehydrogenase electrode of the present invention was prepared in the same manner as Example 1 (A), except that alcohol dehydrogenase (ADH) (EC 1,1,3,4: a product of Sigma Co.) was used instead of GOD and nicotinamide adenine dinucleotide (a product of Sigma Co.) was used instead of benzoquinone.

With this electrode, the cyclic voltammetry was effected in the same manner as Example 1 (B).

Electrolyte

Deoxygenated tris-hydrochloride buffer solution having a pH 8.3
Temperature: 23±1° C.
Stirring rate: 500 r.p.m.

Results

Figure 7:
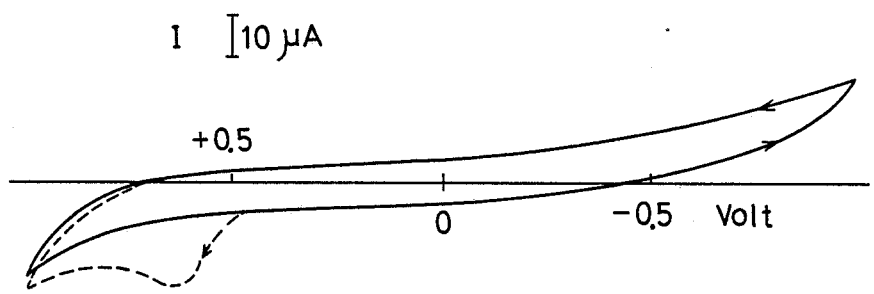
FIG. 7 is a graph showing the cyclic voltammogram pertaining to the alcohol dehydrogenase electrode of Example 4, the full line being for an electrode containing NAD in paste and the broken line being for an electrode containing NADH.

An electrode of the present invention prepared by immobilizing 20 μg of ADH on a graphite paste electrode containing 3% by weight of NAD was immersed in the above-mentioned tris-hydrochloride buffer solution and a cyclic voltammogram was recorded at a potential scan rate of 50 m V/s. The results obtained are shown by the solid line in FIG. 7.

The results were same as the voltammogram recorded in the same manner with respect to an electrode similar to the above one, but not containing NAD.

On the other hand, it was found that an electrode containing NADH, i.e. a reduced type NAD, gave an anodic wave having a peak at +0.6 V as shown by the broken line in FIG. 1. Thus, it was found that only NADH, which is a reduced type of NAD, showed electrochemical response at a carbon paste electrode. That is, it was found that NADH was irreversibly oxidized electrochemically at a paste electrode, according to the equation:

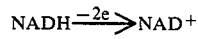

$$NADH \xrightarrow{-2e} NAD^+$$

and eventually NAD could be regenerated at the present electrode.

Electrochemical Catalytic Oxidation of Ethanol

As ethanol was added to the above-mentioned buffer solution, an increase of anodic current was noted at a positive potential higher than +0.6 V. It was found that, with increasing the ethanol concentration in the solution measured, the steady-state current Is increased. It was found that the steady-state current increased also depending on the amount of NAD in the graphite paste and on the amount of ADH on the surface of the electrode.

These results indicate that the immobilized ADH retains its activity and so the NAD entrapped at the interface between the immobilized ADH and the paste electrode acts as electron acceptor in the enzyme reaction of ADH and is reduced to NADH, and that NAD is regenerated electrochemically from such NADH and that as a result of these reactions the steady-state current appears.

Figure 8:
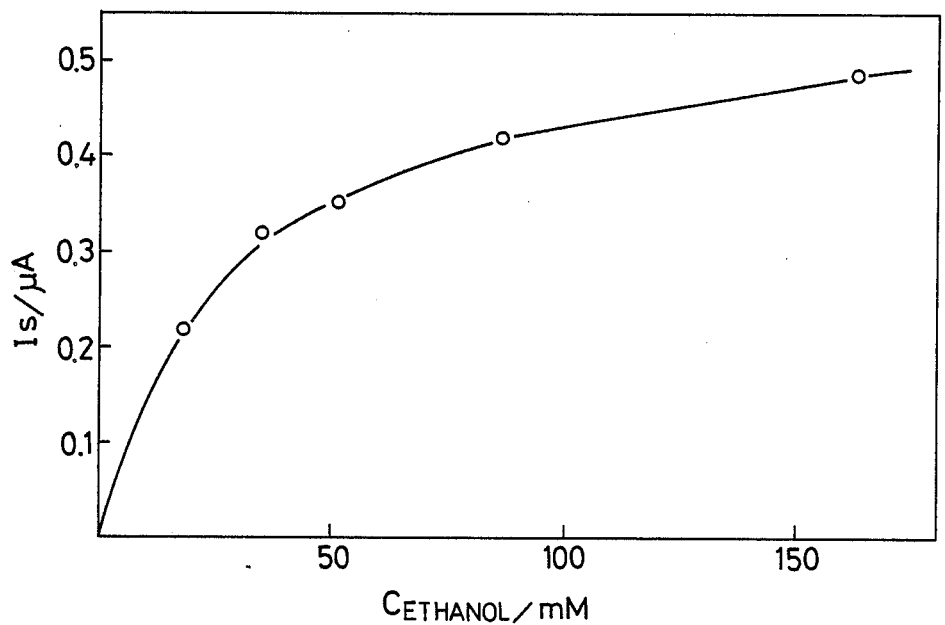
FIG. 8 is a graph showing the relation between the steady state current Is and the ethanol concentration in the solution measured in Example 4.

The dependency to ethanol concentration of Is at an impressed voltage of 0.8 V (against a saturated calomel electrode) of an electrode prepared by immobilizing 20 μg of ADH in a NAD (3% by weight)/graphite paste is shown in FIG. 8. This figure can be used as a calibration curve on measuring by means of the present electrode the ethanol concentration in the solution measured. The present electrode shows a linear response, at an ethanol concentration lower than 10 mM. The response of current is fast, and the steady-state current value is reached within 20 seconds.

EXAMPLE 5

Glucose Dehydrogenase Electrode)

A glucose dehydrogenase electrode the same as that shown in FIG. 4 was prepared in the same manner as Example 1(A), except that glucose dehydrogenase (GDH: a crude extract specimen isolated from *Pseudomonas fluorescens*) was used instead of ADH in Example 4 and dichlorophenolindophenol (DCIP: a product of Nakarai Chemical Co.) was used instead of NAD. The electrode was washed several times with distilled water and immersed and stored overnight in an acetate buffer solution of pH 5.0 before it was used.

Figure 9:
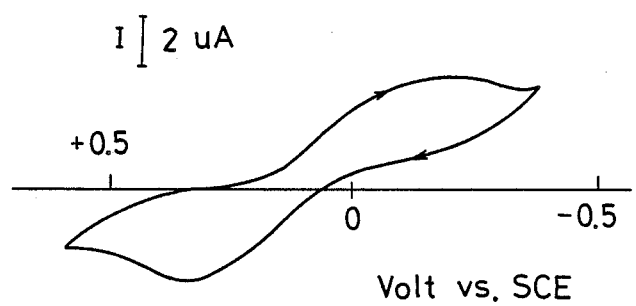
FIG. 9 is a graph showing the cyclic voltammogram of the glucose dehydrogenase electrode of Example 5.

Voltammetry by three-electrode method was effected using this electrode in the same manner as Example 1(B). That is, an electrode of the present invention prepared by immobilizing 100 μg of GDH on a graphite paste electrode containing 3% by weight of DCIP was immersed in an acetate buffer solution having a pH 5.0 and the cyclic voltammogram was recorded at a potential scan rate of 50 m V/s. The results are shown in FIG. 9. The peak was noted at −0.2 V for the cathodic wave, and at +0.3 V for the anodic wave.

When glucose was added to the above buffer solution, an increase of anodic current was observed at a positive potential higher than 0.4 V. It was found that the steady-state current Is increased as the glucose concentration in the solution measured was increased. Further, it was also found that the current Is increased in dependence on the content of DCIP in the graphite paste electrode and the amount of GDH on the surface of electrode.

Figure 10:
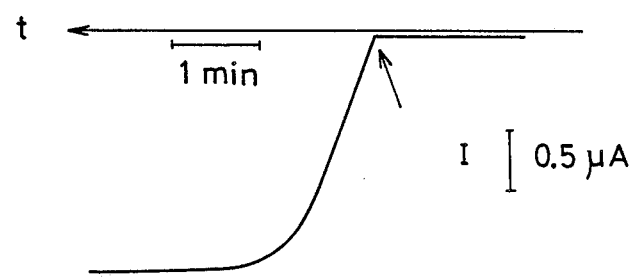
FIG. 10 is a graph showing the responsibility between glucose concentration and anode current.

The characteristic response at this electrode to glucose concentrations in the solution measured is shown in FIG. 10. It was found that the anodic current at +0.5 V began to increase when 10 mM glucose was added to the solution measured (the arrow in the figure) and the steady-state current was reached after about 1 minute.

EXAMPLE 6

A GOD electrode was prepared using gold powder instead of the graphite powder used in Example 1.

At first 0.1 ml of liquid paraffin was added to 0.1 g of gold powder, the mixture was well mixed in an agate mortar, and then 40 mg of p-benzoquinone was further added to the mixture and the resulting mixture was well mixed. The p-benzoquinone/gold paste thus obtained was packed into one end of a glass tube having an inner diameter of 3.4 mm, and the surface of the paste was smoothed with a piece of wax paper.

A GOD electrode same as that shown in Fig. was prepared in the same manner as Example 1.

Figure 11:
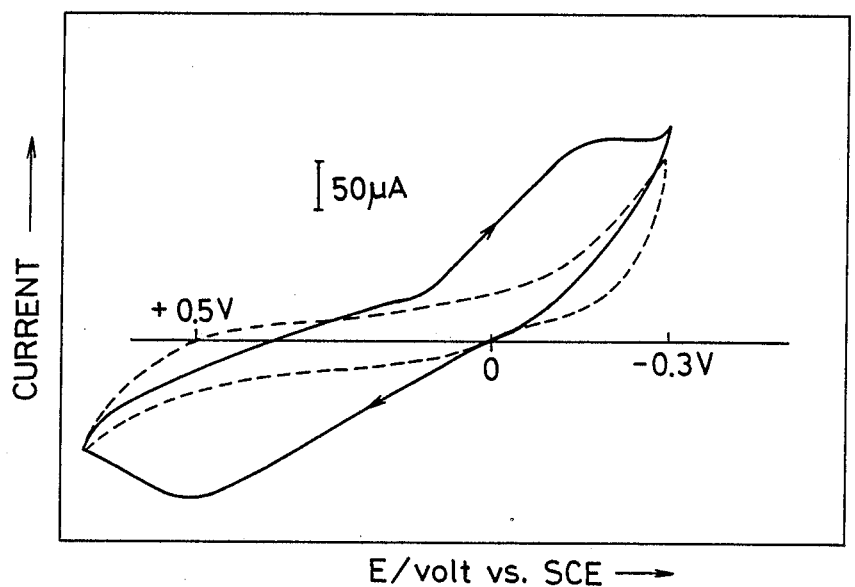
FIG. 11 is a graph showing the cyclic voltammogram pertaining to the enzyme electrode of Example 6.

This electrode was immersed in an acetate buffer solution of a pH 5.0, and the cyclic voltammogram was recorded at a potential scan rate of 50 m V/S. As shown by the solid line in FIG. 11, the peak cathodic and anodic waves were observed at −0.07 V and +0.40 V (vs SCE), respectively. Any decrease of current was not observed even when the cyclic potential scan was continued further for several hours. Although the same evaluation as above was effected with regard to an electrode similar to the above one, but not containing p-benzoquinone, any voltammetric peak was not observed as shown by the broken line in FIG. 11.

Electrocatalytic Oxidation of Glucose

Figure 12:
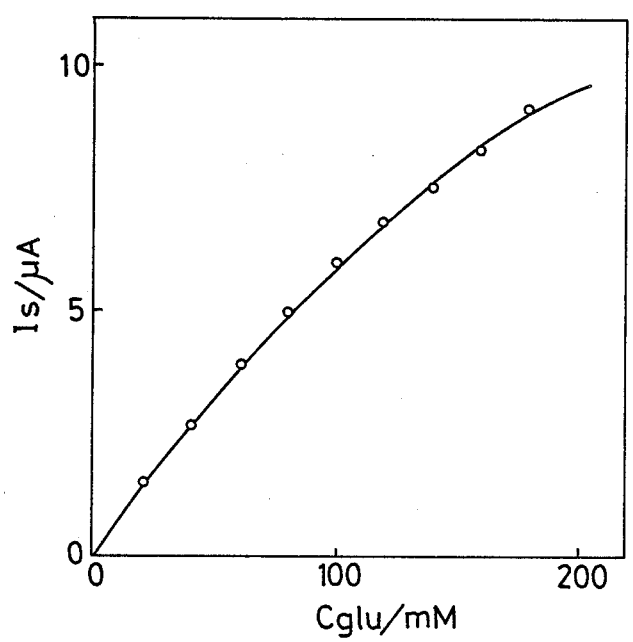
FIG. 12 is a graph showing the responsiveness of the substrate.

By setting a positive potential well higher than the redox potential of p-benzoquinone (E= +0.5 V vs. Ag/AgCl) and adding glucose successively to the above buffer solution to increase the glucose concentration (0→200 mM), the increase of the current from the base was measured. The results are shown in FIG. 12.

From the results, it were found that the electrode of the present invention could correspond even to a minute variation in glucose concentration and so was useful as an electrode for measuring glucose.

The same results as above were obtained also when powder of other metal (such as platinum), semi-conductor (such as titanium oxide, tin oxide, etc.) or high molecular conductor (such as polypyrrole, polyacetylene, etc.) was used instead of the above gold powder.

EXAMPLE 7

A porous graphite plate (RVC 2×1×100 mm, INF, a product of Chemotronix Co.) was used as the carrier.

First, a cylinder having a diameter of 3.4 mm was cut out by a cork borer from the porous graphite plate and a lead wire was connected to one end of the cylinder with a conductive bonding agent. To prevent immersion of solvent, an epoxy bonding agent was applied to the whole surface where the lead wire was adhered, and at the same time said surface was adhered to a glass tube having an inner diameter of 3.4 mm. Then, insulation of the side surface of electrode and fixation of electrode were effected by means of a heat shrinkable tube. The pores of the porous electrode thus prepared were impregnated with a quinone-containing material to form a storage layer (the carrier of the present invention). The quinone-containing material was prepared by mixing 40 mg of p-benzoquinone with 0.3 ml of liquid paraffin in a mortar.

Next, 10 μl of GOD (1 mg/ml) was supplied onto the surface of the storage layer and then water was evaporated. Thereafter, the surface was covered with nylon net, and 20 μl of a collodion/ethanol (¼V/V) mixture was spread on the surface and dried to form a thin nitrocellulose film on the surface of electrode. The nylon net was fixed to the electrode with parafilm, while applying grease to the nylon net at the portion not covering the surface of electrode.

The electrode (100) for measuring glucose, obtained as described above, is shown in FIG. 13. In this figure, (22) denotes the storage layer, (23) the immobilized GOD layer, (24) the thin nitrocellulose layer, (25) the lead wire (platinum wire), (26) the glass tube, (27) the nylon net, (28) the heat shrinkable tube, (29) the conductive bonding agent and (20) the epoxy resin, respectively.

The electrode (100) was washed several times with distilled water and stored overnight in an acetate buffer solution of pH 5.0, before it was used.

Figure 14:
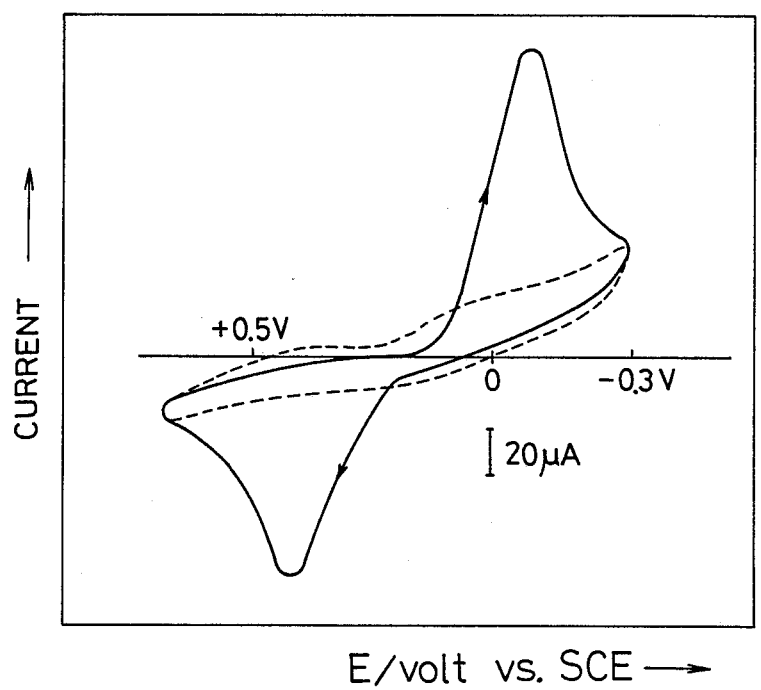
FIG. 14 is a graph showing the cyclic voltammogram pertaining to the enzyme electrode of Example 7.

The electrode was immersed in the above-described acetate buffer solution and the cyclic voltammogram was recorded at a potential scan rate of 50 m V/s, in the same manner as described above. Peaks in cathodic and anodic waves were observed at −0.07 V and +0.40 V (vs SCE), respectively, as shown by the solid line in FIG. 14. Any decrease of current was not observed as the cyclic potential scan was continued further for several hours. As a similar electrode not containing p-benzoquinone was evaluated in the same manner as above, any voltammetric peak was not observed as shown by the broken line in FIG. 14.

Electrocatalytic Oxidation of Glucose

Figure 15:
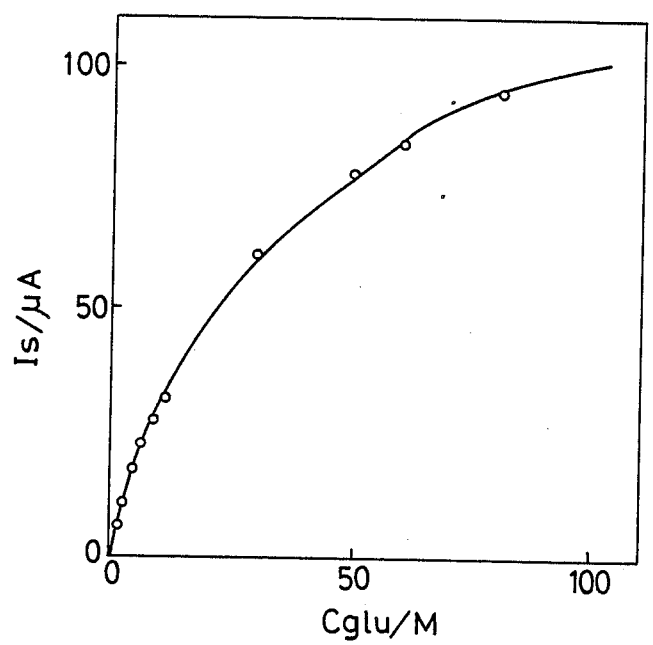
FIG. 15 is a graph showing the responsibility to the substrate.

By setting a positive potential well higher than the redox potential of p-benzoquinone (E= +0.5 V. vs. Ag/AgCl) and adding glucose successively to the above buffer solution to increase its concentration (0→100 mM), the increase of the current from the base was measured. The results are shown in FIG. 15.

From the results, it was found that the electrode of the present invention could correspond even to a minute variation in glucose concentrations and so was useful as an electrode for measuring glucose.

EXAMPLE 8

GOD electrodes were prepared in the same manner as Example 7, using the following materials instead of the quinone-containing material in Example 7, and their responsiveness to glucose was evaluated.

The results are shown in the following table:

TABLE

| Storage layer (impregnating graphite) | p-Benzoquinone (mg) | Dispersant | (ml) | Agent for mixing paste | (mg) | Base E = 0.5 V (μA) | Response to 20 mM glucose (μA) |
| --- | --- | --- | --- | --- | --- | --- | --- |
| Gel containing | 40 | Liquid | 0.3 | Gelol D | 25 | 72 | 128 |

TABLE-continued

| Storage layer (impregnating graphite) | p-Benzoquinone (mg) | Dispersant | (ml) | Agent for mixing paste | (mg) | Base E = 0.5 V (μA) | Response to 20 mM glucose (μA) |
| --- | --- | --- | --- | --- | --- | --- | --- |
| quinone dissolved Quinone teflon paste | 20 | paraffin ®Valflon paste | | | 200 | 2.35 | 0.60 |
| Quinone silicone grease | 10 | Silicone grease | 100 | — | | 0.19 | 0.06 |
| Quinone nujol cellulose | 20 | Liquid paraffin | 0.15 | Cellulose powder | 100 | 0.32 | 1.33 |
| Quinone vaseline | 20 | White vaseline | 200 mg | — | | 0.09 | 1.28 |
| Quinone cemedine | 40 | ®Cemedine-C | 400 mg | — | | 48.5 | 2.0 |
| Quinone nujol carbon powder | 40 | Liquid paraffin | 0.3 | Carbon | 500 | 0.30 | 31.20 |

EXAMPLE 9

A GOD electrode was prepared by using a mini-grid electrode as the internal electrode.

Electrode Material

Gold mini-grid electrode: No. MG-42, 500 wires/in. a product of Buckbee-Mears. Co.

At first, 0.3 ml of liquid paraffin was added to 500 mg of graphite powder and mixed in a mortar, and then 40 mg of p-benzoquinone was added to and uniformly mixed with the resulting mixture. The mixture so obtained was packed into a glass tube having an inner diameter of 3.4 mm and the surface was smoothed with a piece of wax paper to form the storage layer (the carrier). Next, 10 μl of GOD solution was placed on the storage layer and the solvent was removed by evaporation, and then the above gold mini-grid electrode was placed and fixed by nylon net on the resulting storage layer. Further, 10 μl of GOD solution (1 mg/ml) was placed on the gold mini-grid electrode through the nylon net and the solvent was made to evaporate. Then, after 20 μl of a collodion/ethanol solution (1:4) was placed on the electrode and dried, the mini-grid electrode was connected with the lead wire by means of a conductive bonding agent to give an electrode (110) shown in FIG. 16.

Figure 13:
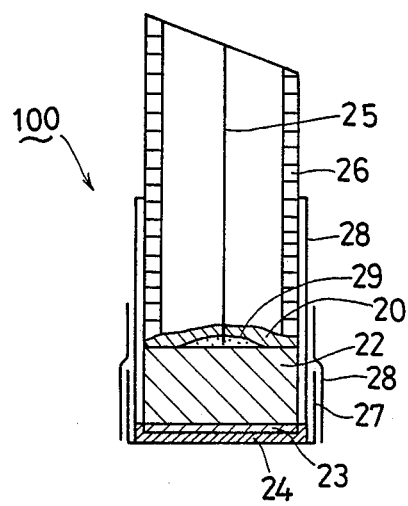
Figure 16:
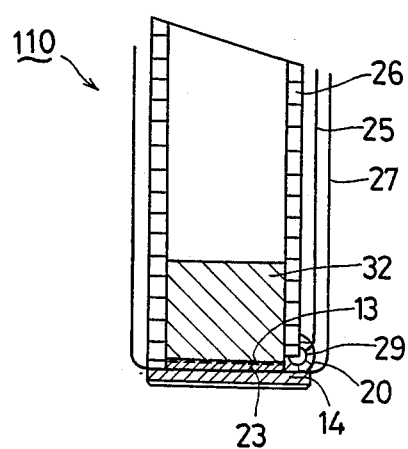

Numeral figures are common to FIG. 16 and FIG. 13. In FIG. 16, (32) denotes the storage layer, (13) denotes the gold mini-grid electrode and (14) denotes the collodion film.

The electrode (110) was stored in the same manner as Example 1 until it was used.

Cyclic Voltammetry

Figure 17:
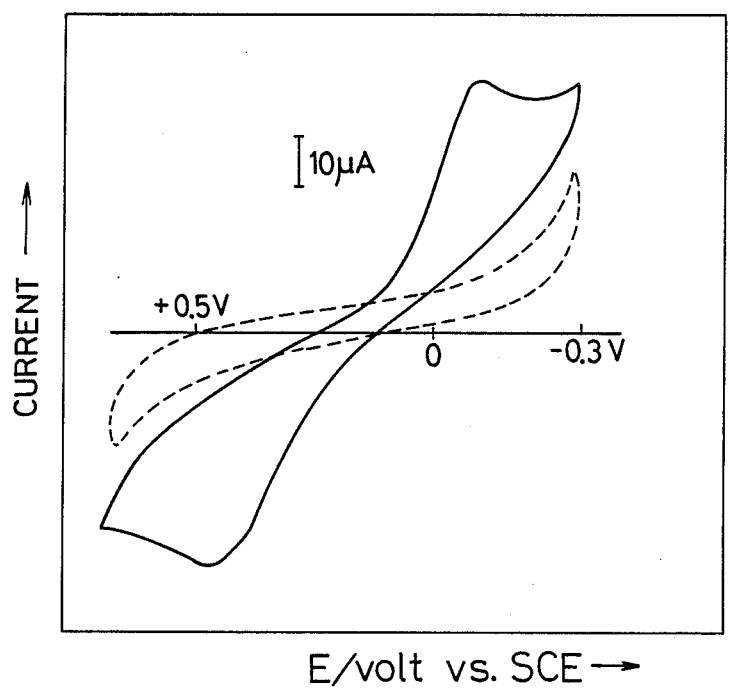
FIG. 17 is a graph showing the cyclic voltammogram pertaining to the enzyme electrode of Example 9.

As the cyclic voltammetry was effected under the same measuring conditions as Example 7, the results shown in FIG. 17 were obtained. As shown in FIG. 17, it was found that, also in the electrode of this Example, p-benzoquinone moving from the storage layer acted as the electron transfer mediator.

Electrocatalytic Oxidation of Glucose

In the same manner as Example 7, the increase of the current from the base was measured by adding glucose successively to the buffer solution to increase its concentration.

Figure 18:
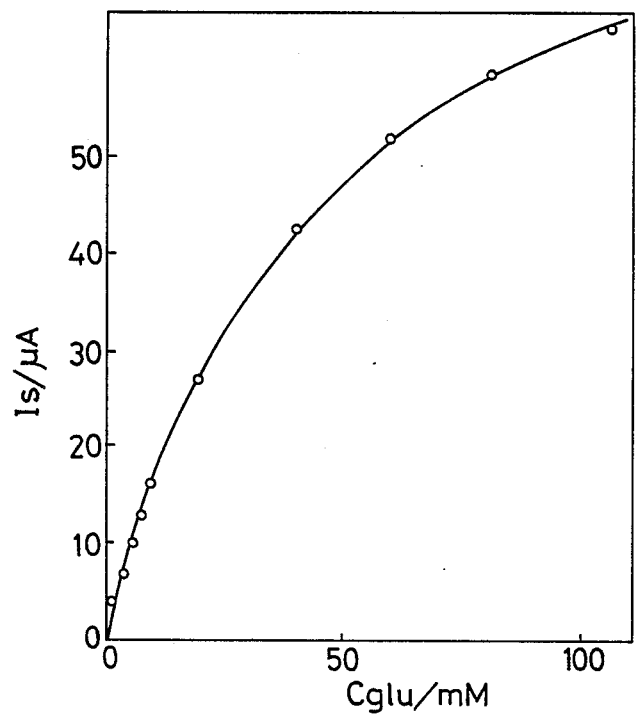
FIG. 18 is a graph showing the responsiveness of the substrate.

The results are shown in FIG. 18. It was found from the results that the above electrode could respond even to a minute variation in glucose concentrations and so was useful as an electrode for measuring glucose.

Also when a mini-grid electrode was used, the same results as above were obtained with respect to various storage layers mentioned in Example 8. The mini-grid electrode could be a metal mini-grid electrode other than the gold mini-grid electrode, such as a platinum mini-grid electrode. It was suitable to compose the mini-grid electrode with a noble metal.

Example 10

Figure 19:
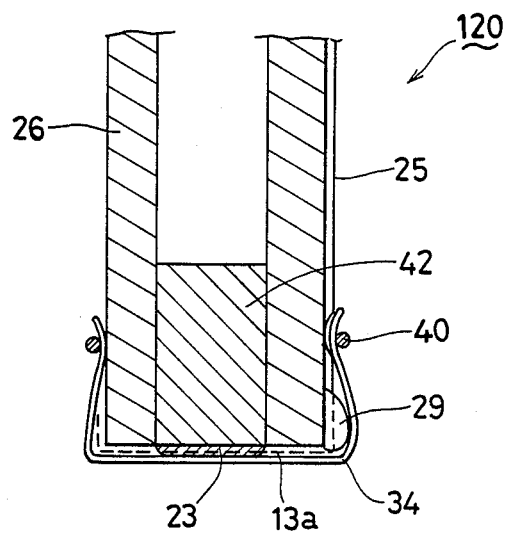
FIG. 19 is a diagram showing the construction of the enzyme electrode of Example 10.

In a mortar, 100 mg of cellulose powder, 200 μl of liquid paraffin (nyjol) and 48 mg of benzoquinone were mixed together. The resulting mixture was packed into one end of a glass tube having an inner diameter of 3.4 mm and an outer diameter of 5 mm, and the surface was smoothed by means of a piece of paraffin paper. On the surface of the paste carrier, a platinum net electrode (100 mesh) cut 5 mm square was placed and a lead was connected to a part of it with a conductive bonding agent. Then, the net portion protruding from the glass tube was turned up and fixed by shielding with an epoxy bonding agent. On the carrier surface where the net electrode was laminated, 5 μl of GOD solution (100 mg/ml) was placed. The surface was covered further with a dialysis film (0.025 mm, a product of Visking Co.) and the dialysis film was fixed with O-ring, whereby an enzyme electrode (120) of the present invention as shown in FIG. 19 was obtained. In FIG. 19, (13a) denotes the platinum net electrode, (23) denotes the immobilized GOD layer, (25) the lead wire, (26) the glass tube, (29) the epoxy bonding agent, (34) the dialysis film, (40) the O-ring, and (42) the paste carrier, respectively.

Figure 20:
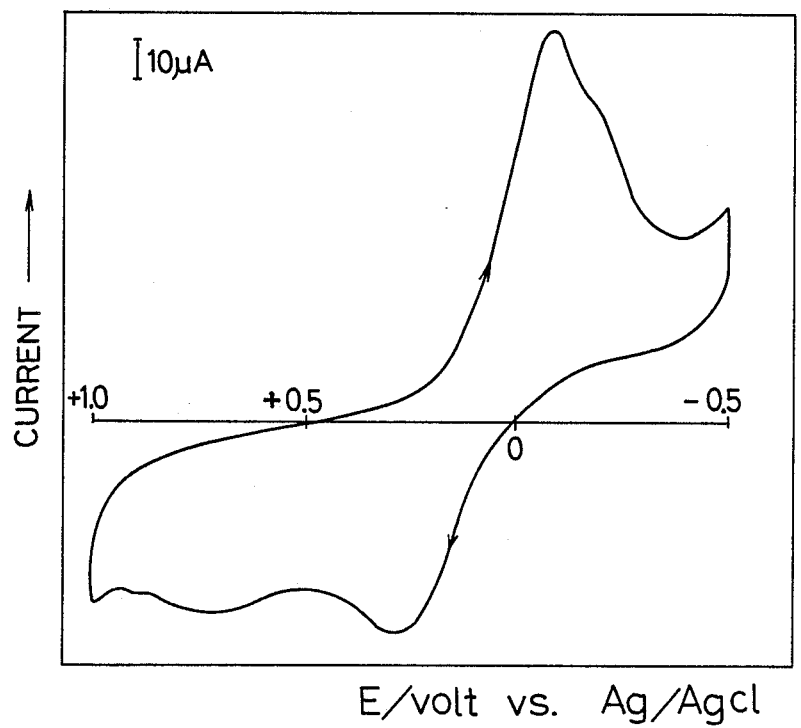
FIG. 20 is a graph showing the cyclic voltammogram pertaining to the enzyme electrode of Example 10.

After leaving the electrode to stand overnight, measurement was effected. At first, the cyclic voltammogram was recorded in a deoxygenated sodium phosphate buffer solution having a pH of 7.0, using a silver-/silver chloride electrode as the reference electrode. As shown in FIG. 20, the reduction wave of benzoquinone was observed at −80 mV and the oxidation wave of hydroquinone at +300 mV.

Figure 21:
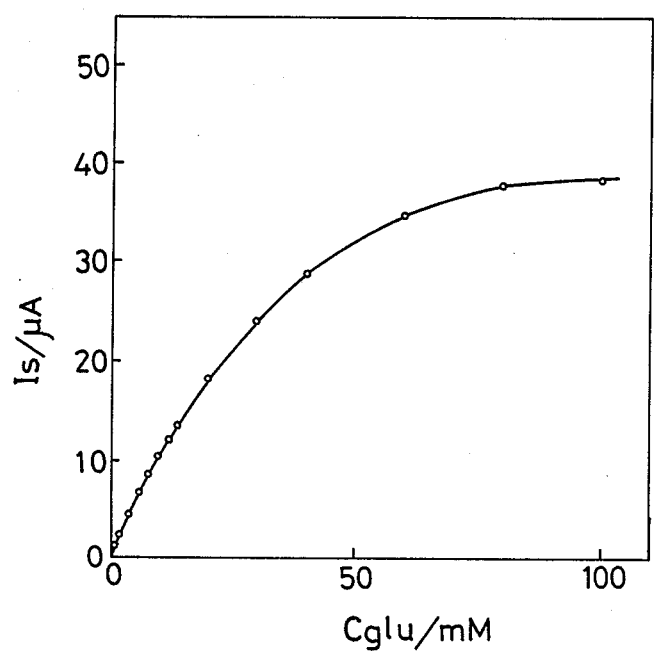
FIG. 21 is a graph showing the responsiveness of the substrate.

Next, by fixing potential at E=450 mV (vs Ag-/AgCl) and adding glucose to the above deoxygenated sodium phosphate buffer solution (25° C.) having a pH of 7.0 under nitrogen stream, a catalytic increase of current was confirmed. The relation between the increase of current and the concentration of glucose added is shown in FIG. 21. Thus, it was found that estimation could be effected up to a high concentration of glucose.

The enzyme electrode of the present invention shows a high current response to the substrate such as glucose, ethanol or the like, without any other electron transfer mediator added into the solution measured. Therefore, the electrode can suitably be used as sensor for various substrates. Further, it is not affected substantially by any variation in oxygen partial pressure even when oxygen is present. Moreover, the ceiling phenomenon of measured values at high concentration region, which has been observed in the oxygen electrodes hithertofore used for measurement of glucose and which results from shortage of oxygen, can be solved by the electrode of the present invention.

Further, the enzyme electrode of the present invention has a merit that the electron transfer mediator is hardly consumed by reaction since the electron transfer mediator reduced by oxidation reaction is regenerated (re-oxidized) by electrode reaction.

In addition, the electrode of the present invention can maintain the high enzyme reactivity of dehydrogenases almost constant over a long period (usually, more than one week), because a graphite paste electrode is used containing a larger amount of electron accepting compounds such as NAD as compared with hithertofore used NAD immobilized dehydrogenase electrodes is capable of supplying said compounds always to the enzyme immobilized layer.

What is claimed is:

1. An enzyme electrode including a carrier, said carrier comprising:
   (a) a storage layer impregnated with a substance capable of functioning as an electron transfer mediator;
   (b) an enzyme-immobilized layer, positioned adjacent to said storage layer, containing an immobilized enzyme;
   (c) a thin film coating said enzyme-immobilized layer permeable to a substrate for said enzyme; and
   (d) an internal electrode capable of applying voltage to said enzyme-immobilized layer.

2. The enzyme electrode as defined by claim 1, wherein said storage layer comprises a material selected from the group consisting of porous materials, pastes, and gels.

3. The enzyme electrode as defined by claim 2, wherein said material is at least semi-conductive.

4. The enzyme electrode as defined by claim 3, wherein said at least semi-conductive material is selected from the group consisting of graphite, noble metals, high molecular conductors, and inorganic semiconductors.

5. The enzyme electrode as defined by claim 1, wherein said substance capable of functioning as an electron transfer mediator is selected from the group consisting of p-benzoquinones, ubiquinones, potassium ferricyanide, dichlorophenolindophenol, phenazine methosulfate, and nicotinamide adenine dinucleotide.

6. The enzyme electrode as defined by claim 1, wherein said storage layer comprises a paste, said substance capable of functioning as an electron transfer mediator is p-benzoquinone, and said p-benzoquinone is present in said paste in an amount of between about 0.2 and 30 percent by weight.

7. The enzyme electrode as defined by claim 1, wherein said storage layer comprises a paste, said substance capable of functioning as an electron transfer mediator is nicotinamide adenine dinucleotide, and said nicotinamide adenine dinucleotide is present in said paste in an amount of between about 1 and 10 percent by weight.

8. The enzyme electrode as defined by claim 1, wherein said immobilized enzyme is selected from the group consisting of oxidases and dehydrogenases.

9. The enzyme electrode as defined by claim 1, wherein said thin film is selected from the group consisting of cellulose acetate film, nitrocellulose film, K-carrageenan gel film, and polyacrylamide gel film.

10. The enzyme electrode as defined by claim 1, wherein said internal electrode is selected from the group consisting of filamentary electrodes and grid electrodes.

11. The enzyme electrode as defined by claim 1, wherein said immobilized enzyme is an oxidase selected from the group consisting of glucose oxidase, galactose oxidase, alcohol oxidase, cholesterol oxidase, amino acid oxidase, and uric acid oxidase.

12. The enzyme electrode as defined by claim 1, wherein said immobilized enzyme is an dehydrogenase selected from the group consisting of glucose dehydrogenase, glutamate dehydrogenase, alcohol dehydrogenase, lactic acid dehydrogenase, and glycerol dehydrogenase.

13. The enzyme electrode as defined by claim 1, wherein a high enzyme reactivity of said immobilized enzyme is maintained at almost constant level for at least one week.

* * * * *

UNITED STATES PATENT AND TRADEMARK OFFICE
CERTIFICATE OF CORRECTION

PATENT NO. : 4,820,399

DATED : April 11, 1989

INVENTOR(S) : Mitsugi SENDA et al.

It is certified that error appears in the above-identified patent and that said Letters Patent is hereby corrected as shown below:

At column 3, line 24, change "responsibility to" to ---responsiveness of---.

At column 4, line 3, insert ---is--- before "regenerated".

At column 4, line 5, insert ---the--- after "by".

At column 5, line 43, change "suitable" to ---suitably---.

At column 8, line 17, delete "the" before "FIGS.".

At column 9, line 43, change "benzoquinone" to ---p-benzoquinone---.

At column 10, line 35, change "on" to ---in---.

At column 11, line 46, change "the results" to ---these results---.

At column 11, line 46, change "were" to ---was---.

At column 12, line 52, change "the results" to ---these results---.

Signed and Sealed this

Nineteenth Day of October, 1993

Attest:

BRUCE LEHMAN

*Attesting Officer*      *Commissioner of Patents and Trademarks*